United States Patent [19]

Bohn

[11] Patent Number: 5,507,833
[45] Date of Patent: Apr. 16, 1996

[54] HIP REPLACEMENT SYSTEM AND METHOD FOR IMPLANTING THE SAME

[75] Inventor: William W. Bohn, Mission Hills, Kans.

[73] Assignee: Kim-Med, Inc., Kansas City, Mo.

[21] Appl. No.: 314,542

[22] Filed: Sep. 28, 1994

Related U.S. Application Data

[63] Continuation of Ser. No. 833,488, Feb. 10, 1992, abandoned.

[51] Int. Cl.⁶ ........................................................... A61F 2/32
[52] U.S. Cl. ................................................. 623/23; 623/18
[58] Field of Search ............................... 623/16, 17, 18, 623/19, 22, 23

[56] References Cited

U.S. PATENT DOCUMENTS

| | | | |
|---|---|---|---|
| 3,740,769 | 6/1973 | Haboush | 623/22 |
| 3,848,273 | 11/1974 | Frey | 623/23 |
| 4,366,183 | 12/1982 | Ghommidh et al. | 623/16 |
| 4,536,894 | 8/1985 | Galante et al. | 623/16 |
| 4,608,053 | 8/1986 | Keller | 623/23 |
| 4,626,392 | 12/1986 | Kondo et al. | 623/16 |
| 4,673,409 | 6/1987 | Van Kampen | 623/23 |
| 4,718,916 | 1/1988 | Morscher | 623/23 |
| 4,795,472 | 1/1989 | Crowninshield | 623/78 |
| 4,865,603 | 9/1989 | Noiles | 623/18 |
| 4,946,379 | 8/1990 | Berchem | 623/23 |
| 5,081,031 | 1/1992 | Tsilibary et al. | 623/22 |
| 5,116,380 | 5/1992 | Hewka et al. | 623/23 |
| 5,139,522 | 8/1992 | Adrey et al. | 623/23 |
| 5,176,712 | 1/1993 | Homsy | 623/23 |

FOREIGN PATENT DOCUMENTS

| | | | |
|---|---|---|---|
| 0013863 | 8/1980 | European Pat. Off. | 623/22 |
| 0112435 | 7/1984 | European Pat. Off. | 623/23 |
| 059919 | 9/1954 | France | 623/23 |
| 3119130 | 3/1983 | Germany | 623/22 |
| 3322803 | 1/1985 | Germany | 623/22 |
| 3322978 | 1/1985 | Germany | 623/22 |
| 0649913 | 6/1985 | Switzerland | 623/22 |

OTHER PUBLICATIONS

"The P.C.A. Primary Total Knee System" from Howmedica, copyright 1984, certain pages.

"The Rationale, Design Characteristics, & Preliminary Results of a Primary Custom Total Hip Prosthesis", Stulberg, et al. Clinical Ortho., #249, Dec. 1989.

Clinical Orthopaedics & Related Research, "Strategies for Improving Fixation of Femoral Components in Total Hip Arthroplasty", #235, Oct. 1988, Poss, et al.

Bias "Total Hip System" Surgical Technique, Gustilo & Kyle, undated.

"The APR Universal Hip System w/Cancellous Structured Titanium", Intermedics Orthopedics, Lawrence Dorr, copyright 1985, Jul. 1985.

Primary Examiner—David Isabella
Attorney, Agent, or Firm—Hovey, Williams, Timmons & Collins

[57] ABSTRACT

A joint replacement system particularly useful in total hip arthroplasty includes a prosthesis presenting a macrotextured dimpled surface thereon for promoting biological fixation of the prosthesis to the surrounding bone. The prosthesis may be, for example, a femoral prosthesis which is designed for insertion along the intramedullary canal of a bone. The femoral prosthesis presents a body portion having a cruciform cross-section and a distal portion which is wide in the coronal plane for conforming to the endosteum of the bone but narrow in the sagittal plane for provide good flexure with the bone. The femoral prosthesis is configured to leave a portion of the intramedullary canal undisturbed to provide better circulation to the bone-growth regions after surgery. The prosthesis may also be an acetabular component having the macrotextured outer surface which permits the shell-like acetabular component to be thinner and also to avoid the necessity of pins or screws ordinarily required to attach an acetabular component to the acetabulum of the pelvis. The invention further includes a novel method of implanting the prosthesis which includes leaving a portion of the intramedullary canal intact rather than reaming out the intramedullary canal to receive the prosthesis as is conventional.

8 Claims, 3 Drawing Sheets

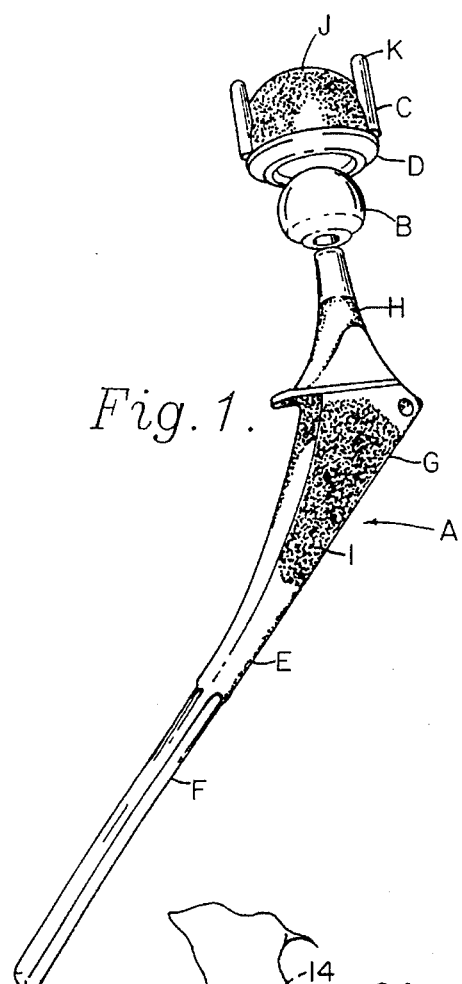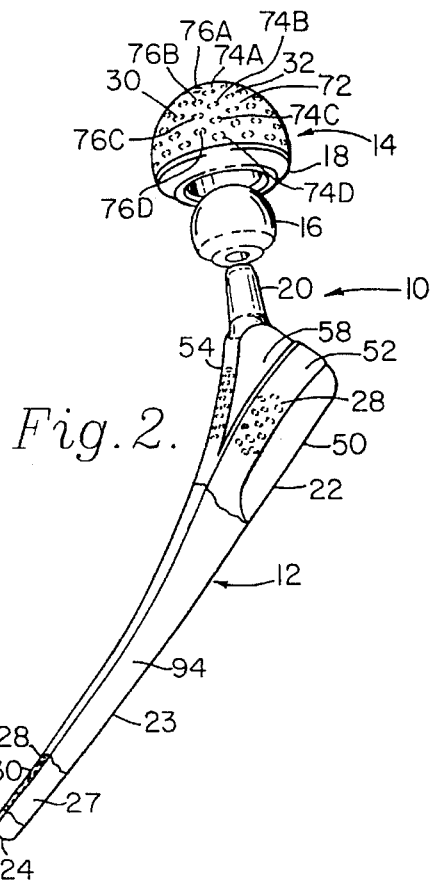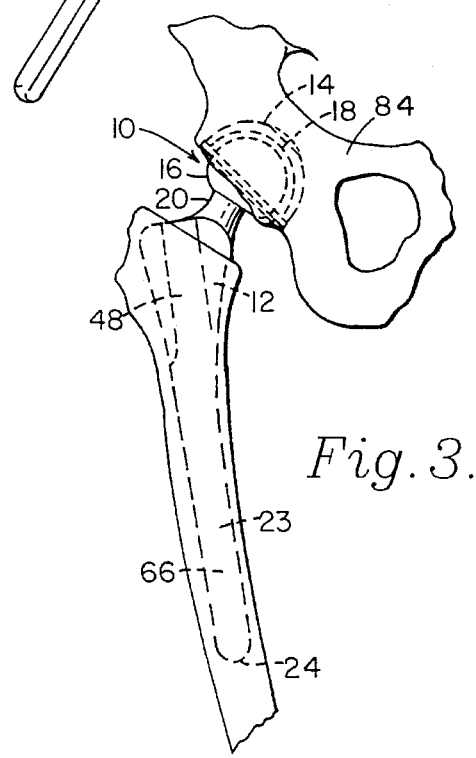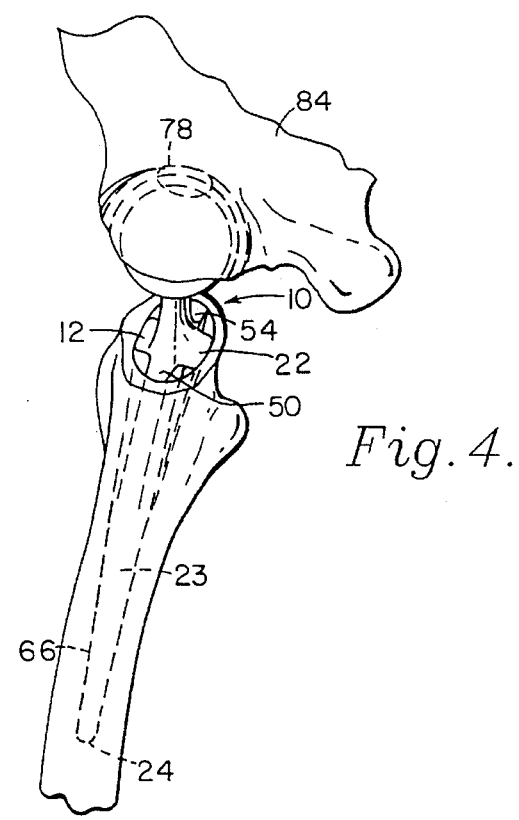

HIP REPLACEMENT SYSTEM AND METHOD FOR IMPLANTING THE SAME

This application is a continuation of application Ser. No. 07/833,488, filed Feb. 10, 1992, now abandoned.

BACKGROUND OF THE INVENTION

1. Field of the Invention

This invention concerns a joint replacement system including a prosthesis having a novel exterior surface configuration for improved fixation within the surrounding bone. In preferred embodiments, the system includes a femoral prosthesis and a complimentary acetabular component which optimize the biological fixation of the bone during post-operative osteogenesis.

2. Description of the Prior Art

Many patients have enjoyed the benefits of joint replacement surgery wherein an artificial joint is substituted for a degenerate or damaged biological joint. This type of surgery is particularly prevalent in the hip joint, where often the preoperative patient experiences substantial pain in even the routine task of walking. The hip joint replacement operation is typical of joint replacement operations, in that the bone comprising the existing joint is removed and a hip replacement system including a femoral component and an acetabular cup (together with a friction-resistant insert) are substituted. Such surgery is commonly referred to as total hip arthroplasty.

This type of surgery requires a great deal of time in the operating theater. Before the surgeon can begin the process of implanting the replacement components, he or she must first make a posteriorlateral incision, retract or dissect the covering musculature, dislocate the hip, and remove the femoral head. The acetabulum must also be reamed out to receive the acetabular cup, and the femur drilled and reamed to receive the femoral component. The greater the amount of bone removed from the medullary bone space, the more effort will be required and the more stress placed on the surrounding bone during surgery. Therefore, prostheses which "fill the medullary bone space" may cause femoral crack or complete fracture during insertion. When the prosthesis fills the medullary bone space, the surgeon loses the margin for sizing error. In addition, when little or no cancellous bone is left, blood vessels are lost and bone regeneration to the prosthesis is limited.

One trend which has developed is the use of a "custom" cementless prosthesis, where biological fixation is employed to hold the prosthesis in place. Custom implants allow the surgeon to tailor the prosthesis to the desired length, diameter, and curvature of the patient to enhance the fit and function of the joint replacement. Uncemented implants appear preferable in patients placing more stress thereon, such as heavier patients, those which are more active and younger patients which will have an implant over a greater length of time. In order to be successful, uncemented implants must achieve long-term fixation necessary for a pain-free function and positive bone growth around the prosthesis. One preferred method of biological fixation at present is a coating of hydroxyapatite $(Ca_{10}(PO_4)_6(OH)_2)$ which enhances bone fixation to the prosthesis as opposed to the uncoated surface of titanium or stainless steel.

Another problem associated with a cementless prosthesis is stress-shielding. This phenomena occurs when the bone fixes biologically to the tip of the prosthesis shank but the body or proximal portion of the prosthesis remains loose. Over time, the bone may wither away from the proximal portion, leading to weakening and eventual failure of the prosthesis due to loss of bone support and resulting metal fatigue. These problems are not generally encountered in cemented prostheses where the proximal or body portion is initially cemented to the surrounding bone.

One of the most significant stresses encountered by a cementless total hip arthroplasty patient post-operation is climbing stairs. This exercise concentrates the stress at the end of the prosthesis because of the stress riser or concentration developed at that point. This occurs for two reasons: the bone is designed to flex slightly while the prosthesis itself is more rigid, and the cavity created by the surgeon may be larger than the prosthesis, causing some stress concentration.

Typical acetabular components affix to the pelvic bone by pins or screws which are inserted therein. The acetabular component thus relies on the pins to hold it in place. This requires a greater acetabular component "shell thickness" to hold the pins or screws, thereby either requiring more removal of the patient's bone or a smaller thickness of the ultra-high molecular weight polyethylene (UHMPE) insert which has some cushioning properties. The screws are both expensive (being made of titanium or less advantageously of stainless steel) and subject to corrosion.

There has thus developed a need for an improved joint replacement system requiring less time, effort and expense during surgery, providing improved biological and mechanical fixation, creating less stress on the surrounding bone, and leaving a portion of the endosteum or inner cortex of the bone intact to promote the flow of blood and biologic fixation therewithin.

SUMMARY OF THE INVENTION

These and other objects are largely solved by the joint replacement system and method of implantation disclosed herein. While the ensuing discussion concerns a femoral prosthesis and an acetabular prosthesis, hereinafter referred to as an acetabular component for use with the human hip, this application is merely exemplary and the concept of the present invention is equally applicable to other joints and to veterinary applications.

Broadly speaking, the present invention includes a prosthesis having a dimpled, macrotextured surface presenting an array of bone growth affixation sites. The surface covers a portion of the prosthesis and presents a dimpled, golf-ball like surface preferably presenting a plurality of offset rows whereby the regenerated bone will grow into the dimples and help hold the prosthesis in place. In the examples illustrated herein, a femoral prosthesis and acetabular component are illustrated, each presenting the macrotextured surface on at least a portion thereof.

The preferred femoral component is made of titanium or titanium alloy and provided with a cruciform contour upper section which engages with the endosteum or inner cortex tapering to a distal portion. The tip of the distal portion is elongate in the medial-lateral dimension and narrow in the anterior-posterior dimension, permitting enhanced flexion of the prosthesis with the surrounding bone. The cruciform design is employed where the femoral bone is most massive and, rather than "filling the medullary bone space", the cruciform shape reduces the risk of damage to the bone and increases the number of fixation points to significantly reduce micromotion occurrence between the implant and the patient's bone. The cruciform cross-section provides a 4-beam design proximal to the femoral stem which is believed to provide optimal proximal fixation and load transfer. The cruciform design at the upper portion also lessens the cross-sectional area enabling the surgeon to obtain a more precise fit at the crucial points of engagement with the inner cortex without the need for further precise concentration on the interior areas, and presents less work for the cutting broach to perform in shaping the canal for receiving the prosthesis than in conventional bone-filling designs. By this it is to be understood that the cancellous bone within the endosteum is softer and easier to remove than the "hard" bone between the endosteum and the periosteum. Finally, the cruciform design lessens the bulk of the prosthesis and presents a lower modulus of elasticity than conventional designs fostering a more flexible prosthesis which is more flexible and thus more likely to move in concert with the surrounding bone, thus reducing pain. As the cruciform shape tapers down to a thin profile from anterior to posterior when viewed in section, the distal portion of the prosthesis becomes even more flexible during the most common flexing encountered by a patient such as climbing stairs.

In addition, the preferred femoral prosthesis of the present invention includes a hydroxyapetite or other bone-growth promoting coating extending circumferentially around the body portion. The distal portion presents a biogrowth distal segment also providing a hydroxyapetite coating extending longitudinally along a discrete segment thereof and separated from the coated body portion by an uncoated region on the prosthesis shank. The biogrowth distal segment is configured to provide sufficient but not overextensive fixation to ensure that the body or proximal portion is sufficiently biologically affixed to the bone and avoid stress shielding. Thus, the hydroxyapetite coating may extend only along a discrete portion of the medial and lateral edges of the distal portion of the prosthesis for first time total hip replacements, or in revision surgery where bone irregularities may require increased fixation, circumferentially around the distal portion of the prosthesis.

The acetabular component is hemispherical in shape and is relatively thin and shell-like. The macrotextured surface is preferably produced by cold working, this imparting strength to the preferably titanium or titanium alloy acetabular component. The acetabular component can thus be thinner than conventional acetabular cups, and thus a greater thickness of the UHMPE insert can be provided. The acetabular component is provided without the need for pins or screws and is coated with hydroxyapatite to promote bone adherence to the surface for cooperating with the dimples to provide enhanced biological fixation. A hole at the top of the acetabular component provides some relief during its press-fit installation, as well as acting as an affixation point during installation or subsequent removal.

In accordance with the method of the present invention, the surgeon prepares for a total hip arthroplasty in the conventional manner, such as described, for example, in the publication BIAS™ Total Hip System, Surgical Technique by Ramon B. Gustilo, M.D. and Richard F. Kyle, M.D., a copy being furnished herewith and the disclosure thereof incorporated herein by reference. However, instead of using a rasp to completely remove the intramedullary canal, a custom broach corresponding to the shape of the prosthesis is employed, leaving a substantial portion of the cancellous bone intact. The acetabulum is reamed out to a dimension 2 to 4 millimeters smaller than the corresponding depth and diameter of the hemispherical-shaped acetabular component using a single-use reamer. This enables a precise bone preparation and fit. The acetabular component is then press-fit into the reamed area without the use of screws or pins, or the necessary holes in the pelvic bone to receive them. The bone growth to the macrotextured surface provides good biologic fixation which favors an initially superior press fit, long term fixation, and enhanced durability of the UHMPE insert. The hole in the top of the acetabular component improves the press-fit and prevents the acetabular component from "bottoming out" and thus giving better stress loading throughout the arcuate surface. The surgeon then proceeds with the surgery as is conventional and described in the aforementioned publication.

BRIEF DESCRIPTION OF THE DRAWINGS

FIG. 1 is a perspective view of a prior art hip replacement system including a femoral prosthesis, modular head, and acetabular component with ultra-high molecular weight polyethylene insert;

FIG. 2 is a perspective view of the hip replacement system of the present invention including the femoral prosthesis, modular head and acetabular component;

FIG. 3 is a fragmentary front elevational view of a patient's hip showing the hip replacement system hereof implanted into the femur and pelvis with portions shown in phantom;

FIG. 4 is an enlarged, fragmentary perspective view of a patient's hip similar to FIG. 3;

DESCRIPTION OF THE PREFERRED EMBODIMENT

Figure 5:
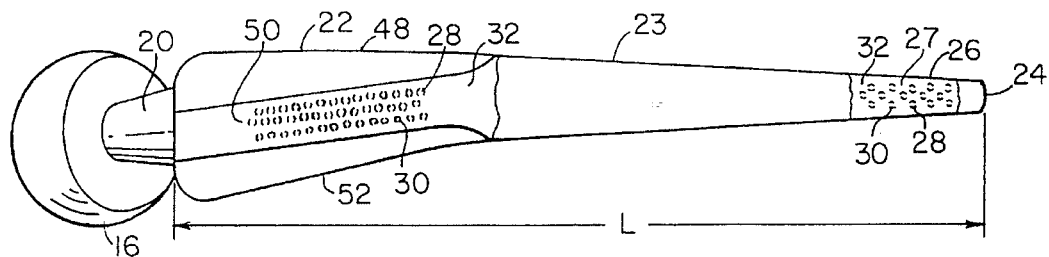
FIG. 5 is an enlarged end elevational view of the femoral prosthesis hereof with the modular head mounted thereon and showing the macrotextured surfaces.

Referring now to the drawing, a prior art hip replacement system is shown in FIG. 1 and includes a femoral prosthesis A, a modular head B, an acetabular component C and an ultra high molecular weight polyethylene (UHMPE) insert D. The femoral component is provided with a shank E including an elongated distal portion F which is cruciform in cross-section and a proximal triangular body G with a Morse taper stem H. Either a fiber metal surface I or mesh is provided on the body G. The acetabular component C is provided with a fiber-metal back surface J and three smooth pegs K integrally formed therewith for load transfer, stability in rotation, and interoperative positioning. Other acetabular components include holes for receiving screws therethrough. The insert D is sized to be snapped into the acetabular cup and to received the modular head B therein.

The hip replacement system 10 in accordance with the present invention is shown in FIGS. 2 through 12 and broadly includes a femoral prosthesis 12 and an acetabular component 14. The prosthesis 12 is adapted to receive a modular head 16 which is conventional and made of cobalt-chrome alloy. The modular head is presently provided in standard diameters of 22, 26, 28 and 32 millimeters, although other sizes could be provided as warranted by the physique of the particular patient. An acetabular liner 18 of UHMPE is provided to fit within the acetabular component 14 and receive the head 16 for ball and socket movement therewithin.

In greater detail, the femoral prosthesis 12 presents a Morse taper stem 20 extending from a proximal body portion 22 which is generally cruciform in cross-section. The body portion 22 gradually tapers to shank 23 presenting tip 24 at the end of distal portion 26 thereof. The distal portion 26 is generally rectangular or oblong in cross-section. The length L of the femoral prosthesis 12 from the proximal body portion 22 to the distal portion 26 is shorter than the prior art prosthesis shown in FIG. 1 in order to minimize loss of bone tissue. For example, the prosthesis shown in FIG. 1 is typically 180 mm in length, whereas the preferred femoral prosthesis 12 in accordance with the present invention is about 100 mm in length.

Figure 12:
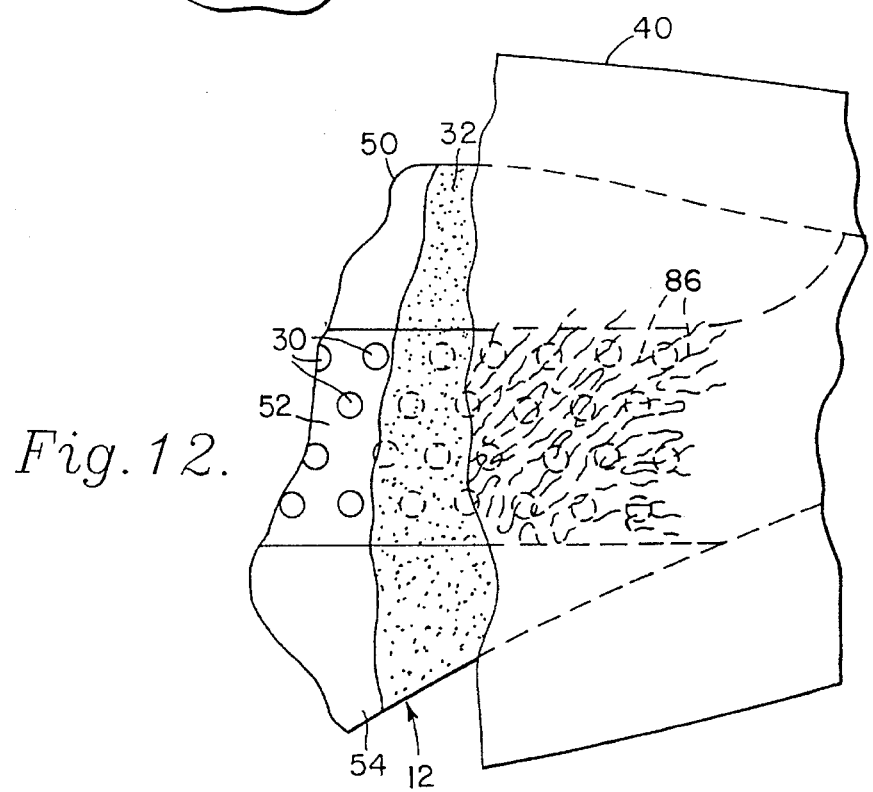
FIG. 12 is an enlarged fragmentary view of the femoral component hereof with lines of bone growth shown extending across the dimpled, macrotextured surface.

Preferably both the body portion 22 and the distal portion 26 are provided with a macrotextured surface 28 characterized by an array of depressions or dimples 30 cold worked into the surface of the prosthesis. Each dimple 30 is preferably circular in shape although it is contemplated that other shapes of depressions could be employed. The dimples 30 are equally sized and about 1 to 3 mm across and no more than about 2 mm deep, with 1 mm being more preferable. The dimples 30 are arrayed in offset columns and rows to provide a staggered array whereby bone will grow into and affix to one or more dimples, as shown in FIG. 12. Typically, the dimples 30 are arrayed in at least two columns 33 and 34, whereby the corresponding rows 35 and 36 are staggered or offset. The femoral prosthesis is preferably provided with a hydroxyapatite coating 32 extending circumferentially around the body portion, and a segment of the distal portion 26 for promoting the growth of bone to the metallic prosthesis 12. An uncoated region 38 may separate the coated portions.

The femur 40 in which the prosthesis is implanted includes the medullary canal 42, the endosteum or inner cortex 44, and the periosteum 46 or outer cortex which surrounds the hard portion of the bone. As shown in FIGS. 5 through 10, at least some of the surfaces of the prosthesis 12 in engagement with the surrounding endosteum or inner cortex 44 are macrotextured with dimples 30 to provide sites for positive fixation of the prosthesis 12 as a result of post-surgical osteogeneration.

Figure 6:
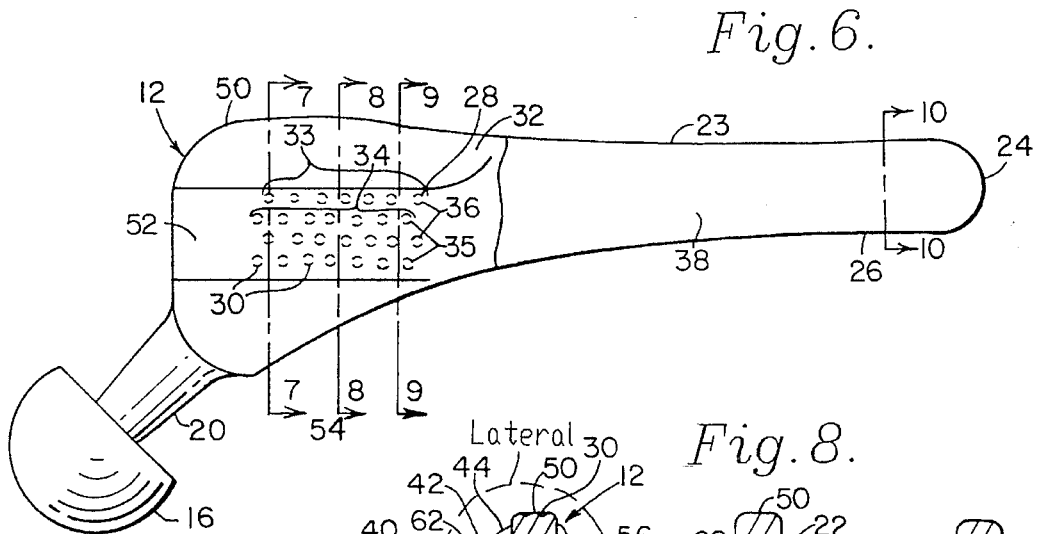
FIG. 6 is an enlarged side elevational view of the femoral prosthesis shown in FIG. 5.
Figure 7:
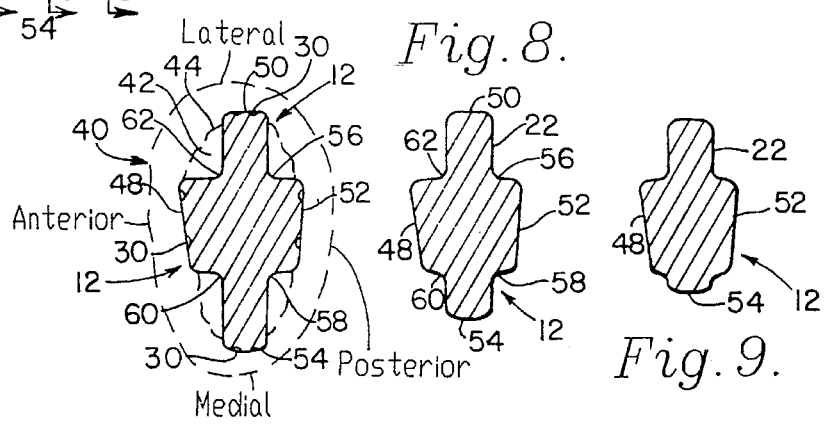
FIG. 7 is a transverse cross-sectional view of the body of the femoral prosthesis taken along line 7—7 of FIG. 6 with the surrounding femur shown in phantom.
Figures 8, 9:
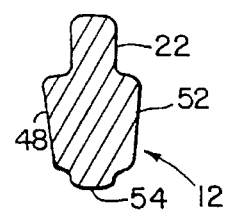
FIG. 8 is a transverse cross-sectional view of the body of the femoral prosthesis taken along line 8—8 of FIG. 6.
FIG. 9 is a transverse cross-sectional view of the body of the femoral prosthesis taken along line 9—9 of FIG. 6.

FIGS. 5 and 6 illustrate the cruciform transverse cross-sectional design of the body portion 22 of the prosthesis 12, further illustrated in the transverse cross-sections thereof shown in FIGS. 7, 8 and 9. Body portion 22 presents four outwardly extending lobes 48, 50, 52 and 54 arranged at generally 90° angles. In the preferred embodiment, the distance the lobes extend varies according to the anatomy of the patient and the prosthesis 12 is customized to conform to the femur 40 of each individual patient. The recesses 56, 58, 60 and 62 between the lobes are generally rounded to limit the stress accumulation during loading caused by walking and other exercise, it being noted that the recesses 56, 58, 60 and 62 are well interior to the endosteum 44 so that a substantial portion of marrow within the medullary canal remains with the patient. Viewing FIGS. 5 through 10, it may be appreciated that the prosthesis tapers from the proximal portion 22 to the tip 24 in the sagittal plane (anterior to posterior) for bending with the femur while remaining relatively wide in a frontal or coronal plane (lateral to medial direction) for providing good fixation to the inner cortex. Thus, at distal portion 26, the prosthesis is oblong or rectangular in cross section presenting medial edge 64, anterior edge 66, lateral edge 68 and posterior edge 70 as shown in cross-section in FIG. 10. Each of the lobes 48, 50, 52 and 54 are macrotextured radially at their furthest surfaces to provide proximal biogrowth segments, as is approximately 2 to 6 cm longitudinally of the medial edge 64 and the lateral edge 68 of the distal portion 26 which engages the endosteum beginning about 2 cm from the stem tip 24.

Figure 10:
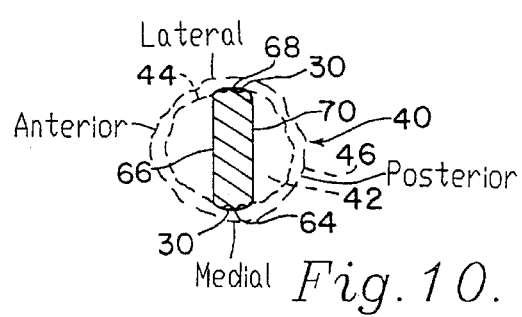
FIG. 10 is a transverse cross-sectional view of the distal portion of the femoral prosthesis taken along line 10—10 of FIG. 6 with the surrounding femur shown in phantom.

The hydroxyapetite coating 32 on distal portion 26 defines a biogrowth distal segment 27. The biogrowth distal segment 27 extends longitudinally approximately 2 to 6 cm and may extend circumferentially around the distal portion 26 as shown in FIG. 2 for improved fixation in revision hip replacements or only on the medial edge 64 and lateral edge 68 as shown in FIGS. 5, 6 and 10 for first-time hip replacements. By separating the biogrowth distal segment 27 from the hydroxyapetite coating which extends circumferentially around body portion 22, by an uncoated region 94, the body portion 22 including lobes 48, 50, 52 and 54 avoids stress-shielding by the distal portion 26 which would otherwise cause metal fatigue and failure in the shank 23 of the femoral prosthesis due to inadequate fixation of the body (or proximal) portion 22 to the surrounding bone.

The acetabular component 14 is substantially hemispherical in shape and is provided with an outer surface 72 which is macrotextured and provided with dimples 30 in much the same manner as a golf ball. The dimples 30 again are preferably 1 to 3 mm in diameter and no greater than 2 mm deep, and more preferably about 1 mm in depth. The dimples are arranged in a staggered array, as shown in FIG. 2, with adjacent rows 74 (comprised of dimples 74A, 74B, 74C and 74D) and 76 (comprising dimples 76A, 76B, 76C and 76D) of dimples 30 being offset as shown. Hydroxyapetite coating 32 preferably covers outer surface 72. The acetabular component 14 is shell-like in configuration and is preferably about 2 to 4 mm in thickness.

Figure 11:
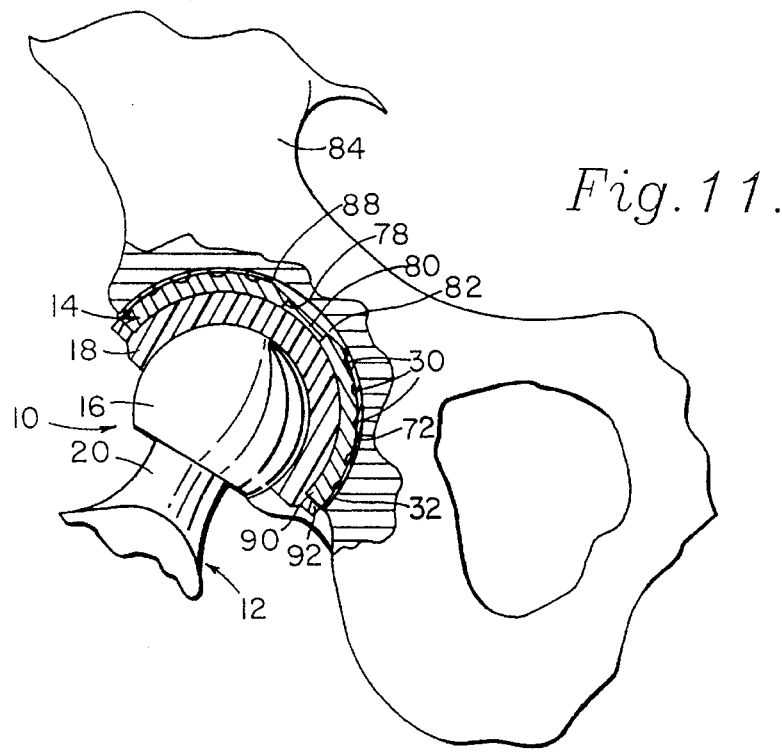
FIG. 11 is an enlarged fragmentary view of the femoral component with the acetabular component hereof shown in section and located in the reamed-out acetabulum of the patient.

As shown in FIG. 11, acetabular component 14 defines a hole 78 which is provided with an internal thread 80 is provided at the center of the acetabular component 14. The opening widens to a dished-out portion 82 to resist bottoming out of the acetabular component 14 against the pelvis 84.

The procedure for implanting the hip replacement system 10 hereof is largely conventional and set forth, for example, in the booklet entitled BIAS™ Total Hip System, Surgical Technique, by Ramon B. Gustilo, M.D. and Richard F. Kyle, M.D., with some variations. For example, the use of the reamer shown in FIGS. 7 and 8 of the Bias™ Total Hip System, as well as the powered flexible reamer usage shown in FIG. 18 thereof, are omitted. The hip replacement system 10 preferably includes a custom femoral component 12 particularly configured for the individual patient. In this manner, the surgeon uses X-rays and other diagnostic tools to prescribe a femoral component 12 which is tailored to the femur 42 and pelvis 84 of the individual patient. It is to be understood that standard sized femoral prostheses 12 in accordance with the present invention will be satisfactory, but that improved results will often be obtained if a custom prosthesis is provided. Rather than using conventional reamers and broaches, a single use broach, that is a broach designed exactly to conform to the prosthesis and for use with only a single patient, is used to provide an exact fit of the femoral prosthesis 12 within the femur 42. Similarly, the acetabular component 14 can be configured for the individual patient and a single use reamer is employed to ream out a cup-shaped hollow 88 in the patient's pelvis 84 corresponding to the arcuate surface of the acetabular component, but slightly smaller to ensure a good press-fit. The opening 78 and adjacent dished-out portion are substantially centrally located, i.e. substantially equidistant from all locations around the circumferentially extending marginal edge 90 of the acetabular component 14 which engages the annular lip 92 of the insert 18.

The configuration of the femoral prosthesis 12 presents a smaller portion which engages the hard bone surrounding the inner cortex, and thus it is easier for the surgeon to broach out the opening to receive the prosthesis 12. This enables the surgeon to make a more exact fit as he is less exhausted and prone to error. The cruciform body design provides excellent stability and still leaves a portion of the marrow occupying the medullary canal intact to leave blood passages open for osteogenesis. The single use broach which conforms exactly to the shape of the femoral prosthesis 12 with regard to the portion engaging the bone thus need not disturb the remainder of the medullary canal and inner cortex, thus shortening the time spent in preparing the femur for insertion of the prosthesis.

A single use reamer is employed to ream the acetabulum to a dimension approximately 2 mm less than the diameter across the acetabular component 14, so that a good press fit is ensured. The opening in the top of the acetabular component 14 also provides a relief for some of the compression and aids in providing a good press fit, as well as avoiding "bottoming-out" during subsequent activity by the patient. Moreover, the thinness made possible by the cold-working of the acetabular component enables the surgeon to remove a lesser amount of bone from the pelvis 84 than with conventional components, and no additional drilling is required to provide sites in the pelvis 84 for receiving pins, screws and the like. The surgeon then press-fits the UHMPE insert 18 into the shell-like acetabular component 14. After the modular head 16 is press-fitted to the stem 20, the entire hip replacement system is fitted together and the surgeon proceeds with the surgery as is conventional.

Post-operation, the bone of both the pelvis 84 and femur 42 begins to grow. As the particular pattern of bone growth cannot be anticipated, the bone growth is along some random patterns according to the stress placed on the bone-prosthesis interface as illustrated by the random bone growth lines 86 shown in FIG. 12. Both the outer surface 74 of the acetabular component 14 and the body and distal portions of the femoral prosthesis 12 are coated with hydroxyapatite, and the bone grows onto the portions of each. Particularly beneficial is the macroengagement and fixation made possible by the dimpled surfaces, which provides a biogrowth topography to maximize bone-prosthesis fixation and durability of the interface. By arranging the dimples in columns and rows, the bone growth is more likely to engage at least one, and possibly two or more dimples 30. Rather than using horizontal or vertical ridges which require anticipation of the bone growth patterns, the dimples 30 enable a plurality of small sites for receiving bone growth therein. Thus, the bone is able to "decide for itself" the vector of growth it will address in the remodeling process. The growth of bone into the dimples 30 further strengthens the hydroxyapatite-metal interface and lessens the likelihood that the hydroxyapatite coating will be sheared away from the metal and thus it is believed that the regenerated bone thus actually serves to hold the coating to the metal.

While the preferred embodiment of the above invention has been cast in reference to a hip replacement system in referring to the preferred embodiment, it is to be understood that the invention could be readily employed in both human and veterinary applications, and for other joints besides the hip. In any location where biological fixation is desired between a joint replacement component and the surrounding bone, the principles taught by the invention disclosed hereof may be employed. For that reason, the scope of the invention shall be determined by the following claims and not limited to the specific embodiment and application disclosed hereinabove.

We claim:

1. A prosthesis for surgical implantation into a bone, comprising:

an elongated shank having a surface and said shank extending between proximal and distal ends, said shank having a relatively wide proximal end and an opposed, relatively narrow distal end, said proximal end having a generally cruciform cross-section with four circumferentially spaced radially extending lobes each including a respective bone engaging surface, said distal end having a generally rectangular cross-section with a pair of opposed, relatively wide distal-defining surfaces and a pair of opposed, relatively narrow distal-defining surfaces;

a first plurality of depression formed in at least a portion of said bone engaging surface;

a second plurality of depressions formed in at least a portion of said distal-defining surfaces of said distal end, each of said depressions being discrete, non-linear and spaced from adjacent depressions on said body and configured for enhancement of bone-prosthesis fixation, the surface of said shank between the first and second plurality of depressions being essentially smooth and free of depressions.

2. A prosthesis for surgical implantation into a bone as set forth in claim 1 said first and second plurality of depressions having a minimum dimension of about 1 mm and a maximum dimension of about 3 mm.

3. A prosthesis for surgical implantation as set forth in claim 1 wherein said first and second pluralities of depressions are provided by cold-working the surface of the prosthesis.

4. A prosthesis for surgical implantation as set forth in claim 1 wherein said first and second pluralities of depressions are arrayed in at least two adjacent columns.

5. A prosthesis for surgical implantation as set forth in claim 4 wherein said first and second pluralities of depressions in one of said columns are staggered relative to the depressions in an adjacent column.

6. A prosthesis for surgical implantation as set forth in claim 1, said bone engaging surfaces tapering into said elongated shank.

7. A prosthesis for surgical implantation as set forth in claim 1, said first and second plurality of depressions being coated with a bone growth promoting material.

8. A prosthesis for surgical implantation as set forth in claim 1, said depressions being in the form of dimples which are essentially circular in plan configuration, with a diameter of from about 1–3 mm and a depth of up to about 2 mm.

\* \* \* \* \*